United States Patent [19]

Jaoua et al.

[11] Patent Number: 5,686,295
[45] Date of Patent: Nov. 11, 1997

[54] PROCESS FOR THE GENETIC MANIPULATION OF MYXOBACTERIA

[75] Inventors: Samir Jaoua, Villa Mounir Sfax, Tunisia; Thomas Schupp, Möhlin; Snezana Neff, Bubendorf, both of Switzerland

[73] Assignee: Novartis Finance Corporation, New York, N.Y.

[21] Appl. No.: 276,752

[22] Filed: Jul. 18, 1994

Related U.S. Application Data

[63] Continuation of Ser. No. 841,680, Feb. 26, 1992, abandoned.

[30] Foreign Application Priority Data

Mar. 1, 1991 [CH] Switzerland .................. 626/91

[51] Int. Cl.$^6$ .................. C12N 1/21; C12N 15/63
[52] U.S. Cl. .................. 435/252.3; 435/320.1; 536/23.1; 536/23.7; 536/24.1
[58] Field of Search .................. 435/69.1, 172.1, 435/172.3, 252.3, 320.1; 536/23.1, 23.7, 24.1

[56] References Cited

U.S. PATENT DOCUMENTS 4,910,140 3/1990 Dower .................. 435/172.3

FOREIGN PATENT DOCUMENTS

| | | |
|---|---|---|
| 0317509 | 5/1989 | European Pat. Off. . |
| 0358606 | 3/1990 | European Pat. Off. . |
| 0372230 | 6/1990 | European Pat. Off. . |
| WO87/07909 | 12/1987 | WIPO . |

OTHER PUBLICATIONS

Norton, "Microbiology" 2nd Ed. Addison–Wesley Pub. Co. 1986, pp. 253–255.
Breton et al., *J. Bacteriol.*, 161:523–528 (1985).
Breton et al., *J. Biotechnol.*, 4:303–311 (1986).
Breton et al., *FEMS Microbiol. Lett.*, 40:183–188 (1987).
Datta et al., *J. Bacteriol.*, 198:1244–1249 (1981).
Denhardt, *Biochem. Biophys. Res. Comm.*, 23:641–646 (1976).
Hedges et al., Plasmid, 2:269–278 (1979).
Gentz et al., *PNAS USA*, 78:4926–4940 (1981).
Jaoua et al., Plasmid, 18:111–119 (1987).
Jaoua et al., *Plasmid*, 23:183–193 (1990).
Kaiser, Genetics of Myxobacteria, in: *Myxobacteria: Development and Cell Interactions*, ed. by E. Rosenberg, (Berlin/New York:Springer Verlag, 1984), pp. 163–184.
Kuner et al., *PNAS USA*, 78:425–429 (1981).
Kuspa et al., *J. Bacteriol.*, 171:2762–2772 (1989).
Maniatis et al., *Molecular Cloning*, New York:Cold Spring Harbor Laboratory, 1982.
Miller, *Experiments in Molecular Genetics*, New York:Cold Spring Harbor Laboratory, 1972.
Murray et al., *Mol. Gen. Genet.*, 150:53 (1977).
O'Conner et al., *J. Bacteriol.*, 155:317–329 (1983).
Rella, Dissertation ETH Zurich, No. 7601, SFITZ.
Reichenbach et al., *Trends in Biotechnology*, 6:115–121 (1988).
Rigby et al., *J. Mol. Biol.*, 113:237–251 (1977).
Rosenberg et al., *Ann. Rev. Genetics*, 13:319–353 (1979).
Shimkets et al., PNAS USA, 80:1406–1410 (1983).
Simon et al., Bio/Technol., 784–791 (Nov. 1983).
Shimkets et al., *Mol. Gen. Genet.* 211: 63–71 (1988).

*Primary Examiner*—David Guzo
*Attorney, Agent, or Firm*—J. Timothy Meigs

[57] ABSTRACT

The present invention relates to a novel process for the genetic manipulation of myxobacteria, preferably of myxobacteria of the Sorangium/Polyangium group, which makes it possible for the first time specifically to apply recombinant DNA techniques to this group of organisms. The technical implementation of this process is based primarily on the preparation of recombinant DNA molecules which, by reason of their specific construction, are able to integrate genes or DNA sequences which code, where appropriate, for novel and desirable properties, with the aid of homologous recombination at sites, which are accurately defined by reason of the homologies present, within the bacterial genome, and on the insertion thereof into the myxobacterial cell.

12 Claims, No Drawings

PROCESS FOR THE GENETIC MANIPULATION OF MYXOBACTERIA

This application is a continuation of application Ser. No. 07/841,680, filed Feb. 26, 1992, now abandoned.

The present invention relates to a novel process for the genetic manipulation of myxobacteria, preferably of myxobacteria of the Sorangium/Polyangium group, which makes it possible for the first time specifically to apply recombinant DNA techniques to this group of organisms.

In particular, the present invention relates to a process for the insertion of DNA sequences of homologous or heterologous origin or a combination of DNA sequences of homologous or heterologous origin into the chromosome of said myxobacteria via homologous recombination, and to genetically modified myxobacteria prepared with the aid of this process.

Likewise embraced are recombinant DNA molecules, plasmids and vectors which are particularly suited for use in the process according to the invention, and genetically modified myxobacteria of the Sorangium/Polyangium group containing exogenous DNA of homologous and/or heterologous origin.

The myxobacteria of the Sorangium/Polyangium group are highly specialised organisms which are commonly detectable in soil samples, dead plant material or in animal dung. Characteristic of this group of microorganisms is their ability to utilise cellulose or cellulose-containing degradation products as sole carbon source. Another characteristic feature of this group is their ability to produce highly active secondary metabolites.

A large number of strains from this group which, for example, are able to synthesise plant-microbicidal compounds have now been described. Particularly important in this connection are the so-called soraphens, macrocyclic compounds which have a beneficial biocidal spectrum against phytopathogenic microorganisms, but especially against phytopathogenic fungi. These compounds have very advantageous curative, systemic and, in particular, preventive properties and can be employed to protect numerous crop plants [EP 0 358 606].

It is also known of other representatives of the group of myxobacteria that they are able to synthesise highly active compounds with antibiotic potency [Reichenbach et al (1988)]. Because of the importance of these compounds, there is a great interest in understanding the genetic bases of their synthesis in order thus to provide the possibility of being able specifically to influence these where appropriate.

The precondition for this is the provision of a process which makes possible direct, and preferably targeted, manipulation of these organisms using recombinant DNA techniques, for example by the targeted incorporation of novel genes or gene fragments or other DNA sequences, including whole plasmids, into the genome of the myxobacteria.

A few representatives of the group of myxobacteria have already been the subject of investigations in this direction. Special interest in this connection was primarily directed at *Myxococcus xanthus*, which is a myxobacterium which has now been extensively researched and for which various gene transfer processes have already been described. Thus, for example, the coli phage P1 has been used very intensively, initially for the insertion of transposon Tn5 into the *Myxococcus xanthus* chromosome [Kaiser (1984); Kuner and Kaiser (1981)] and then later for the transfer of genes cloned in *Myxococcus xanthus* back into the original *E. coli* host [O'Conner and Zusman (1983); Shimkets et al (1983)].

Another process for gene transfer is based on the use of the plasmid RP4 which has a very wide host range. Breton et al (1985) were able to show that this plasmid can be transferred via conjugation from *E. coli* into *Myxococcus xanthus*, and is there stably integrated into the chromosome. Based on these properties, Breton et al (1986) and Breton and Guespin-Michel (1987) were able to integrate foreign genes into the chromosome of *Myxococcus xanthus*. Investigations by Jaoua et al (1987; 1989) revealed that the observed integration is based, with a high degree of probability, on a so-called site specific recombination. The latter is confined to particular sites, which have a narrow spatial restriction, within the *Myxococcus xanthus* chromosome and is mediated by one or more so-called hot spots on the RP4 plasmid. In addition, it has emerged during the investigations carried out within the scope of the present invention that the previously known Myxococcus system discovered here cannot be applied to bacteria of the Sorangium/Polyangium group. It is assumed that these organisms lack the specific structural elements which are necessary for site specific recombination on their chromosomes. In addition, it has been found that no stable transposition takes place with these organisms either, for example on use of transposon Tn5.

The object which it was intended to achieve within the scope of this invention thus related primarily to the provision of a universally applicable process for the genetic manipulation of all myxobacteria, but especially of myxobacteria of the Sorangium/Polyangium group, which is free of the abovementioned restrictions of the known processes and thus permits undirected or else, preferably, targeted insertion of genetic material into myxobacteria, independent of structural elements present on the myxobacterial chromosome or of specific transposition events.

This can be achieved according to the invention, for example, by preparing genetic constructs, especially plasmid vectors, which, by reason of their specific structure, can be inserted at the desired sites within the chromosome and which are not linked, as is the case in the previously known processes, to particular integration sites predetermined by the functional organisation of the myxobacterium chromosome or of the plasmid used (hot spots), or else dependent on transpositions of integrated transposons.

The present invention thus relates primarily to a process for the genetic manipulation of bacteria of the order Myxobacterales, but especially of myxobacteria of the Sorangium/Polyangium group, which is characterised in that genetic material of homologous or heterologous origin or a combination of genetic material of homologous and heterologous origin is inserted into the myxobacterial cell and integrated, via homologous recombination at random or else, when there is appropriate knowledge of the structural and functional organisation of the bacterial genome, specifically at a site, which is accurately defined on the basis of the homology present between the inserted DNA and DNA intrinsic to the myxobacteria, into the chromosome of said myxobacteria, independent of structural elements present on the myxobacterial chromosome or of specific transposition events.

The process according to the invention for the genetic manipulation of bacteria of the order Myxobacterales is particularly characterised in that (a) genetic material of homologous or heterologous origin or a combination of genetic material of homologous and heterologous origin, which naturally contains one or more DNA sections which are homologous with or else at least essentially homologous with a corresponding region on the myxobacterial chromosome; or else (b) genetic material which naturally contains no sections which are homologous with or else at least essentially homologous with a corresponding region on the myxobacterial chromosome and which is therefore artificially linked to such homologous or else essentially homologous DNA sections using rDNA techniques known per se; is inserted into the myxobacterial cell and there integrated, via homologous recombination, at a site, which is accurately defined by reason of the homologies present between inserted DNA and DNA which is intrinsic to the bacteria, into the chromosome of said myxobacteria, independent of structural elements present on the myxobacterial chromosome or of specific transposition events.

The integration of the genetic material into the bacterial chromosome via homologous recombination is mediated by one or more DNA sections within the DNA to be inserted, which are homologous with or else at least essentially homologous with a corresponding region on the myxobacterial chromosome. It is thus not bound to the presence of particular chromosomal structures and can in principle take place at any desired site within the bacterial chromosome.

The homologous DNA sections which can be used within the scope of the process according to the invention do not necessarily have to have 100% identity with the corresponding sections on the myxobacterial chromosome in order to be able to bring about the required recombination event. On the contrary, it suffices for these DNA sections to be essentially homologous with the corresponding regions on the bacterial genome, that is to say when these have a degree of homology of between 60% and 100%, preferably between 80% and 100% and very particularly preferably between 90% and 100%.

Thus, "homologous" DNA sections are intended also to mean hereinafter those sections which do not have 100% identity with the corresponding regions on the myxobacterial chromosome but are at least "essentially homologous" therewith.

It is possible in this connection for the homologous DNA sections to be isolated either from the target organism itself or else from related organisms, for example after fragmentation of the particular genome. When the DNA sequence of the DNA sections on the myxobacterial chromosome which are intended in each case to be used for integration is known, the corresponding DNA fragments which are homologous with or else at least essentially homologous with these chromosomal sections can, of course, also be prepared by synthesis.

The DNA sections of homologous origin which can be used within the scope of the present invention can moreover be either DNA sections of known sequence or else DNA fragments obtainable at random, for example after restriction digestion of homologous DNA.

When the structural and functional organisation of the appropriate parts of the myxobacterial genome is known, the process according to the invention thus makes possible for the first time a targeted, predictable modification of the genes present on the myxobacterial genome (in situ modification) by exchange of natural or artificially modified genes, gene fragments or other useful DNA sequences with homologous DNA sections within the bacterial genome. The process according to the invention furthermore makes possible a specific identification of the function of individual genes within the complete genome of myxobacteria by specific switching off of genes [gene disruption] or by complementation of genes which have previously been inactivated by application of other processes, especially of mutation processes.

Besides the targeted and thus very efficient in situ modification of genes intrisic to the bacteria (directed mutagenesis), the process according to the invention has a number of other possible applications such as, for example, the incorporation of additional gene copies in regions known to have a high expression rate, and elimination and thus switching off of unwanted genes. It is furthermore also possible now to think about the following further possible applications.

Incorporation of strong or controllable promoters in front of genes, intrinsic to the bacteria, with interesting functions.

Cloning of genes of various origin into myxobacteria, but especially into myxobacteria of the Sorangium/Polyangium group.

Cloning and expression of genes of various origin.

Transfer of the inserted DNA back into another microorganism such as, for example, into E. coli for further processing.

Use of the heterologous DNA of an inserted vector firstly as radioactive probe for identifying the myxobacterium fragments adjacent to the site of integration, and secondly as pattern [template] for amplification within the scope of a polymerase chain reaction [PCR].

The present invention further relates to a process for the preparation of genetically modified bacteria of the order Myxobacterales, but especially of bacteria of the Sorangium/Polyangium group, which is characterised in that ($a_1$) genetic material of homologous or heterologous origin or a combination of genetic material of homologous and heterologous origin, which naturally contains one or more DNA sections which are homologous with or else at least essentially homologous with a corresponding region on the myxobacterial chromosome; or else ($a_2$) genetic material which naturally contains no sections which are homologous with or else at least essentially homologous with a corresponding region on the myxobacterial chromosome and which is therefore artificially linked to such homologous or else essentially homologous DNA sections unsing rDNA techniques known per se; is inserted into the myxobacterial cell and there integrated, via homologous recombination, at a site, which is accurately defined by reason of the homologics present between inserted DNA and DNA which is intrinsic to the bacteria, into the chromosome of said myxobacteria, independent of structural elements present on the myxobacterial chromosome or of specific transposition events; and (b) positive transformants are selected with the aid of selection processes known per se and cultivated as pure culture.

The present invention thus makes possible for the first time a targeted genetic manipulation of the genome of myxobacteria, but especially of myxobacteria of the Sorangium/Polyangium group, where the integration of the genetic material can be mediated, depending on the particular of aim of the planned procedure, alternatively either by homologous DNA sections of known sequence or else by randomly selected homologous sections of unknown sequence.

The present invention likewise embraces recombinant DNA molecules which, by reason of their specific construction, are able to integrate genetic material such as, for example, genes or gene fragments or other useful DNA sequences which, where appropriate, cede for novel and desirable properties, with the aid of homologous recombination at random or else, when the structural and functional organisation of the bacterial genome is known, also targeted at sites, which are accurately defined by reason of the homologies present between inserted DNA and DNA intrinsic to the bacteria, within the bacterial genome, as well as processes for the preparation of said recombinant DNA molecules.

The present invention furthermore embraces genetically modified myxobacteria, especially modified myxobacteria of the Sorangium/Polyangium group with, where appropriate, novel and/or improved properties, which have been prepared by insertion of said recombinant DNA molecules.

The present invention additionally relates to the offspring of said modified myxobacteria and to mutants and variants thereof which still contain said recombinant DNA molecule.

A number of terms which are customary in recombinant DNA technology and in bacterial genetics are used in the following description.

In order to ensure clear and uniform understanding of the description and of the claims, as well as of the scope intended to apply to said terms, the following definitions are stated:

Gene(s) or DNA of heterologous origin: A DNA sequence which codes for a specific product or products or fulfils a biological function and which originates from a species other than that into which the said gene is inserted; said DNA sequence is also called foreign gene or foreign DNA, or exogenous DNA.

Gene(s) or DNA of homologous origin: A DNA sequence which codes for a specific product or products or fulfils a biological function and which originates from the same species into the which the said gene is inserted. This DNA is also called exogenous DNA.

DNA homology: Degree of agreement between two or more DNA sequences.

Synthetic gene(s) or DNA: A DNA sequence which codes for a specific product or products or fulfils a biological function and which is prepared by a synthetic route.

Promoter: A control sequence of DNA expression which ensures the transcription of any desired homologous or heterologous DNA gene sequence in a host cell, as long as said gene sequence is linked in an operable manner to a promoter of this type and the latter is active in said host cell.

Termination sequence: DNA sequence at the end of a transcription unit which signals the end of the transcription process.

Overproducing promoter (OPP): Promoter which is able to bring about in a host cell the expression of any functional gene sequence(s) linked in an operable manner to an extent (measured in the form of the RNA or of the polypeptide amount) which is distinctly higher than is naturally observed in host cells which are not transformed with said OPP.

3'/5' non-translated region: DNA sections which are located downstream/upstream of the coding region and which, although transcribed into mRNA, are not translated into a polypeptide. This region contains regulatory sequences such as, for example, the ribosome binding site (5').

DNA expression vector: Cloning vehicle such as, for example, a plasmid or a bacteriophage, which contains all signal sequences which are necessary for the expression of an inserted DNA in a suitable host cell.

DNA transfer vector: Transfer vehicle such as, for example, a plasmid or a bacteriophage vector, which makes it possible to insert genetic material into a suitable host cell.

Homologous recombination: Reciprocal exchange of DNA pieces between homologous DNA molecules.

Mutants, variants: Spontaneously or else artificially, by application of known process measures such as, for example, UV treatment, treatment with mutagenic agents etc., produced derivative of a microorganism which still has the features and properties, essential to the invention, of the initial strain which has acquired the latter by reason of the transformation with exogenous DNA.

It has now been possible for the first time within the scope of the present invention to provide a process which makes possible a preferably targeted genetic manipulation of the genome of bacteria of the order Myxobacterales, but especially of bacteria of the Sorangium/Polyangium group, in that it is now possible for genetic material to be integrated, and also to be expressed therein, at random or else, when there is appropriate knowledge of the structural and functional organisation of the bacterial genome, specifically at accurately defined positions, which can be predetermined in some cases, within the bacterial genome, independent of structural elements present on the myxobacterial chromosome or of specific transposition events.

The process according to the invention is, moreover, essentially based on the recognition that it is possible to incorporate exogenous genetic material with the aid of homologous recombination into the genome of myxobacteria, it being possible to use, besides natural, also artifically modified and/or synthetic genes or gene fragments or other DNA sequences including whole plasmids, as long as they comprise DNA sections or are flanked by DNA sections which have a homology, which is sufficient for recombination, with corresponding sections on the myxobacterial genome.

The homologous DNA sections which can be used within the scope of the present invention do not in this connection necessarily have to have 100% identity with the corresponding sections on the myxobacterial chromosome in order to be able to bring about the required recombination event. On the contrary, it suffices if these DNA sections are essentially homologous with the corresponding regions on the bacterial genome, that is to say if these have a degree of homology of between 60% and 100%, preferably between 80% and 100% and very particularly preferably between 90% and 100%.

The size of said homologous regions can vary, but ought to be at least 100 Bp. Regions of homology which comprise between 0.3 Kb and 4 Kb, but preferably between 1 Kb and 3 Kb, are preferred within the scope of this invention.

Recombinant DNA molecules which, by reason of their specific construction, make possible the specific incorporation of genes or gene fragments or other interesting DNA sequences, including whole plasmids, into the genome of a target cell with the aid of homologous recombination in the abovementioned manner form an essential component of the present invention.

The present invention relates in particular to recombinant DNA molecules which make possible a targeted integration of genetic material such as, for example, genes, gene fragments or other DNA fragments at a defined site within the genome of myxobacteria, but especially of myxobacteria of the Sorangium/Polyangium group, and which are characterised in that they contain the DNA which is to be integrated, and in that said DNA has homologies with corresponding DNA regions within the myxobacterial genome, or else is flanked by such homologous DNA sequences, to an extent such that, on transformation of the myxobacterial cell containing the homologous DNA region, there is undirected or else, preferably, targeted integration of said DNA, which is to be integrated, at a site, which is exactly defined by reason of the homology present between the inserted DNA and the DNA intrinsic to the bacteria, within the myxobacterial genome via homologous recombination, independent of structural elements present on the myxobacterial chromosome or of specific transposition events.

Said recombinant DNA molecules can be prepared very straightforwardly in such a way that the DNA which is to be integrated and which has the abovementioned properties (a) is isolated from a suitable source; or (b) when said DNA which is to be integrated naturally contains no sections which are homologous with or else at least essentially homologous with a corresponding region on the myxobacterial chromosome, this DNA is artificially linked with the aid of rDNA techniques known per se to corresponding homologous or else essentially homologous DNA sections.

If the DNA which is to be integrated is an expressible DNA sequence it is advantageous for the latter to be linked in an operable manner to expression signals capable of functioning in the bacterial cell, and, where appropriate, to be flanked by DNA sections which have homologies with a particular region within the bacterial genome. These flanking, homologous DNA sections are present, preferably fused together to a unit, as component of DNA molecules which are closed in the form of a ring.

The latter can be dispensed with if said expressible DNA sequence itself already has sufficiently great homology with corresponding DNA regions within the bacteria/genome so that direct exchange of this DNA sequence for said homologous genomic DNA can take place by means of homologous recombination.

Besides double-stranded DNA, it is also possible to employ in the process according to the invention single-stranded DNA and partially single-stranded DNA.

Suitable for use in the process according to the invention are both homologous and heterologous gene(s) or DNA sequences, as well as synthetic gene(s) or DNA sequences complying with the definition made within the scope of the present invention.

The DNA sequences which are to be integrated can, moreover, be constructed exclusively from genomic, from cDNA or synthetic DNA. Another possibility comprises the construction of hybrid DNA sequences consisting both of cDNA and of genomic DNA and/or synthetic DNA.

In this case, the cDNA can originate from the same gene or DNA section as the genomic DNA or else both the cDNA and the genomic DNA can originate from different genes or DNA sections. In each case, however, it is possible for both the genomic DNA and/or the cDNA, each on its own, to be prepared from the same or from different genes or DNA sections.

If the DNA sequence contains portions of more than one gene or DNA section, these can derive either from one and the same organism, from a plurality of organisms, which belong to various strains, or varieties of the same species or different species of the same genus, or else from organisms which belong to more than one genus thereof or to another taxonomic unit.

In order to ensure the expression of a structural gene in the bacterial cell, it is possible, where appropriate, for the coding gene sequences initially to be linked in an operable manner to expression sequences able to function in the myxobacterial cell.

The expressible hybrid gene constructions of the present invention thus usually contain, besides the structural gene (s), also expression signals which include both promoter and terminator sequences and, preferably, further regulatory sequences of the 3' and 5' non-translated regions.

Every promoter and every terminator which is able to bring about induction of expression of an expressible DNA sequence in myxobacteria can be used as component of the hybrid gene construction.

Examples of promoters suitable for use in the process according to the invention are the light-inducible promoter of Myxococcus xanthus [EP 310 619];

other *Myxococcus xanthus* promoters;

promoters of Actinomycetes, especially of Streptomycetes;

*E. coli* promoters such as, for example, the Tac(hybrid), $P_L$ or Trp promoter.

Suitable termination sequences which can be used within the scope of this invention are described, for example, by Rosenberg and Court (1979) and by Gentz et al (1981).

The functional unit which has been formed in this way and consists of a gene and of expression signals active in myxobacterial cells can subsequently, where appropriate, be flanked by one or more DNA sections which have homologies with corresponding DNA regions within the myxobacterial genome to an extent such that, on transformation of the myxobacterial cell containing said homologous region, there is random or else, preferably, specific integration of a gene sequence which is flanked by homologous DNA sequences at a site, which is defined on the basis of the homologies present between inserted DNA and DNA intrinsic to the bacteria, within the bacterial genome by homologous recombination. The flanking, homologous DNA sections are, moreover, within the scope of this invention present, preferably fused together to a unit, as component of a DNA molecule which is closed in the form of a ring.

In a preferred embodiment, moreover, the DNA which is to be inserted is integrated into a plasmid which either already contains homologous DNA sections or else acquires the latter cloned in at a later time.

Thus, if the intention is to integrate not just single genes or gene fragments but the complete plasmid DNA, which may contain said genes or gene fragments, into the myxobacterial genome, it is sufficient to clone said homologous DNA sequences into the plasmid DNA at a required site, although, where possible, the genes intended for expression should be functionally retained. Thus, it is also possible in this case too for the DNA which is to be integrated (plasmid DNA) to be regarded in principle as flanked by homologous DNA sequences because these homologous DNA sections can be thought of as fused together to a unit within the DNA molecule which is closed in the form of a ring.

Besides structural genes, it is also possible to use any other desirable genes or gene fragments or other useful DNA sequences such as, for example, binding sites of regulator molecules, promoters, terminator sequences etc.

It is now possible for the first time, by the choice of suitable DNA sequences of homologous or heterologous origin, which have sufficiently great homologies with corresponding sections within the bacterial genome and thus allow exchange of genetic material via homologous recombination, for genes or other DNA sequences to be integrated specifically at predetermined sites in the myxobacterial genome and to be expressed there where appropriate.

The extent of the homology, which is necessary for exchange via homologous recombination, between the homologous DNA sections and the corresponding genomic DNA region depends on a variety of parameters and must therefore be adapted to the appropriate needs in each case, depending on the DNA sequences used. It is assumed on the present state of knowledge that a homologous region comprising at least 100 Bp is sufficient to bring about the required recombination event.

A homologous region which extends over a range of 0.3 to 4 Kb, but preferably over a range of 1 to 3 Kb, is preferred within the scope of this invention.

Suitable for use as homologous DNA sections within the scope of this invention are primarily DNA sequences of homologous origin which can be obtained by isolation of the complete myxobacterial DNA and subsequent digestion with suitable restriction enzymes. Where the DNA sequence of said homologous DNA fragments is known they can, of course, also be prepared by synthesis.

However, it is furthermore also possible to use homologous DNA sections of heterologous origin, which have been isolated not directly from the genome of the target organism but, for example, from related organisms and which thus do not necessarily have 100% identity with the corresponding DNA regions on the genome of the target organism but are only essentially homologous with the latter, that is to say have a degree of homology between 60% and 100%, preferably between 80% and 100% and very particularly preferably between 90% and 100%.

An essential component of the present invention is therefore formed by a process for the specific genetic manipulation of bacteria of the order Myxobacterales, which is characterised in that genetic material of homologous origin or a combination of genetic material of homologous and heterologous origin is inserted into the myxobacterial cell and integrated there via homologous recombination specifically at a site, which is accurately defined by reason of the homologies present, into the chromosome of said myxobacteria.

It is thus now possible for the first time within the scope of this invention, by preparing appropriate hybrid gene constructions in the manner described above, to carry out specific modifications of bacteria-intrinsic genes within the myxobacterial genome or else to incorporate additional genes or other DNA fragments into the myxobacterial genome. If the integration takes place within a functional gene or operon, this usually leads to inactivation thereof and, as a consequence, to a phenotypically observable defect.

The specific procedure for this can be such that myxobacterial cells are transformed with one of the recombinant DNA molecules described above, with the genes, hybrid gene constructions or other DNA fragments contained in said recombinant DNA molecule being integrated by homologous recombination randomly or else, preferably, specifically at a site, which is defined by reason of the homologies present and thus can be predetermined, into the bacterial genome.

In a specific embodiment of the present invention, the insertion of the genetic material into myxobacteria, in particular into myxobacteria of the Sorangium/Polyangium group, takes place in an undirected manner via conjugal transfer of plasmid DNA from a donor cell to a Sorangium/Polyangium recipient cell.

The procedure for the preparation of suitable plasmids which have a homology with the myxobacterial chromosome which is sufficient for integration via homologous recombination can be, for example, such that the complete DNA is initially isolated from myxobacteria and subsequently fragmented. This fragmentation can be carded out either mechanically by the action of shear forces or else, preferably, by using suitable restriction enzymes.

It is then possible to isolate from the large number of resulting fragments those of suitable size and subsequently clone them into a suitable plasmid. The ligation of homologous DNA fragments and of DNA fragments of homologous and heterologous origin into a suitable cloning vector is carried out using standard methods as are described, for example, by Maniatis et al, 1982.

This usually entails the vector and the DNA sequence which is to be integrated initially being cut with suitable restriction enzymes. Examples of suitable restriction enzymes are those which provide fragments with blunt ends, such as, for example, SmaI, HpaI and EcoRV, or else enzymes which form cohesive ends, such as, for example, EcoRI, SacI, BamHI, SalI, PvuI etc.

Both fragments with blunt ends and those with cohesive ends, which are complementary with one another, can be linked again, with the aid of suitable DNA ligases, to give a single continuous DNA molecule.

Blunt ends can also be prepared by treatment of DNA fragments which have protruding cohesive ends with the Klenow fragment of $E.$ $coli$ DNA polymerase by filling in the gaps with the appropriate complementary nucleotides.

On the other hand, cohesive ends can also be prepared artificially, for example by attaching complementary homopolymeric tails to the ends of a required DNA sequence and of the cut vector molecule using a terminal deoxynucleotidyl transferase or else by attaching synthetic oligonucleotide sequences (linkers) which carry a restriction cleavage site, and subsequent cutting with the appropriate enzyme.

It is possible in principle to use for the preparation and multiplication of the constructs which have been described above and which contain DNA fragments of homologous or else a combination of DNA fragments of homologous and heterologous origin all conventional cloning vectors such as, for example, plasmid or bacterophage vectors as long as they have replication and control sequences which originate from species which are compatible with the host cell.

The cloning vector usually carries an origin of replication, in addition specific genes which lead to phenotypical selection features in the transformed host cell, especially to resistance against antibiotics. The transformed vectors can be selected on the basis of these phenotypical markers after a transformation into a host cell.

Selectable phenotypical markers which can be used within the scope of this invention comprise, for example, without this representing a limitation on the subject-matter of the invention, resistances to ampicillin, tetracycline, chloramphenicol, hygromycin, G418, kanamycin, neomycin and bleomycin. A prototrophy for particular amino acids can function as further selectable marker, for example.

Preferred within the scope of the present invention are primarily $E.$ $coli$ plasmids such as, for example, the plasmid pSUP2021 used within the scope of the present invention.

Suitable host cells for the cloning described above which are within the scope of this invention are primarily prokaryotes, including bacterial hosts such as, for example, $A.tumefaciens,$ $E.$ $coli,$ $S.$ $typhimurium$ and $Serratia$ $marcescens,$ furthermore pseudomonads, actinomycetes, salmonellae and myxobacteria themselves.

$E.$ $coli$ hosts such as, for example, the $E.$ $coli$ swain HB101 are particularly preferred.

Competent cells of the $E.$ $coli$ strain HB101 are in this connection prepared with the aid of the processes customarily used for the transformation of $E.$ $coli$ [see: "General recombinant DNA techniques"].

Transformation and subsequent isolation on a suitable medium are followed by the resulting colonies being subjected to differential screening by plating out on selective media. It is then subsequently possible to isolate the appropriate plasmid DNA from those colonies which contain plasmids with DNA fragments cloned in.

Recombinant plasmids of different size are obtained in this way. After restriction analysis it is then possible for plasmids of suitable size to be selected for the subsequent insertion of the plasmid DNA into the myxobacterial cell. This DNA transfer can moreover take place either directly or else, preferably, via an intermediate host (donor cell) within the scope of a conjugal transfer.

An essential component of the present invention therefore relates to the construction of plasmids which, besides homologous sections, can also contain one or more gene constructions consisting of one or more structural genes or other desirable genes or gene fragments which are, where appropriate, linked in an operable manner to expression signals able to function in bacterial cells, or other useful DNA sequences. The homologous DNA fragments can in this connection either consist entirely of genome sections which are intrinsic to the bacteria (myxobacteria) and thus are completely of homologous origin, or else they can, besides homologous sections, also contain more or less expressed portions of heterologous origin. The use of homologous DNA sections of purely heterologous origin is also conceivable.

These plasmids can be used in a further process step for insertion of the genetic constructions which have been described above and which contain, where appropriate, a structural gene which codes for a required gene product, into the myxobacterial cell and integration there into the bacterial genome.

The transfer of the genetic constructions according to the application into the myxobacterial cells can be carded out in a variety of ways. Preferred within the scope of this invention is conjugal transfer from a donor cell to the myxobacterial recipient.

It is possible within the scope of this conjugal transfer for the DNA which is to be transferred moreover to be either initially cloned, as described above, in one of the cloning vectors customarily used, and subsequently transformed into a suitable intermediate host which functions as donor cell. The roundabout route via the intermediate host can be avoided by using a host strain which is suitable both for the cloning of DNA and for the use as donor cell within the scope of the conjugation.

Intermediate hosts which can be used within the scope of this invention as donor cells are essentially prokaryotic cells selected from the group consisting of *E. coli*, pseudomonads, actinomycetes, salmonellae and myxobacteria themselves.

The precondition for conjugal transfer of plasmid DNA from a donor cell to a recipient is the presence of transfer (Ira) and mobilisation functions (mob). Moreover the mobilisation function must contain at least the transfer origin (oriT) and be located on the plasmid to be transferred. By contrast, the transfer function (tra) can be either located on the plasmid or on a helper plasmid or else be present integrated into the chromosome of the donor cell.

Plasmids which meet the abovementioned precondition and are therefore preferred within the scope of this invention essentially fall into incompatibility groups P, Q, T, N, W and ColI. The prototype of the P group plasmids is the plasmid RP4. Particularly preferred within the scope of this invention is the plasmid pSUP2021 which contains a 1.9 Kb fragment from the plasmid RP4, which has as component of the mob function (RP4mob) the transfer origin (oriT). Other plasmids with the mob function (RP4mob), such as, for example, pSUP101, pSUP301, pSUP401, pSUP201, pSUP202, pSUP203 or pSUP205, and the derivatives derived therefrom [Simon et al (1988)] can likewise be used within the scope of the process according to the invention.

During the course of the experiments carried out within the scope of this invention it has emerged that it is advantageous when the myxobacterial recipient is exposed to a brief heat treatment during the course of the conjugal transfer before the incubation with the donor strain. A preincubation of the recipient cell at a temperature of 35° C. to 60° C., preferably at a temperature of 42° C. to 55° C. and very particularly preferably at a temperature of 48° C. to 52° C. for one to 120 minutes, but in particular 5 to 20 minutes, is preferred.

Used in a preferred embodiment of the present invention is an *E. coli* donor strain which contains the transfer genes (tra) of plasmid RP4 incorporated into the chromosomal DNA. Preferred within the scope of this invention is the *E. coli* donor strain W3101(pME305) which contains the helper plasmid pME305 which has the transfer function (Ira) of RP4.

Particularly interesting for the process technique, and thus particularly preferred within the scope of this invention, are bacterial strains which are suitable both as hosts for cloning of vectors with integrated DNA sequences and for use as donor cell within the scope of the conjugal transfer. Likewise particularly preferred are bacterial strains which are restriction-negative and thus do not degrade inserted foreign DNA. Both of the abovementioned criteria are met by the *E. coli* strain ED8767(pUZ8) in an ideal manner, but this is mentioned at this point only as representative of other suitable bacterial strains and is not intended to limit the application in any way.

Besides the conjugal gene transfer, described above, from a donor cell into a myxobacterial recipient, it is, of course, also possible to use other suitable gene transfer processes for inserting genetic material into myxobacteria. Mention may be made here primarily of gene transfer via electroporation, within the scope of which the myxobacterial cells are briefly exposed to high electric field strengths [Kuspa and Kaiser (1989)]. The general outline conditions for electroporation of prokaryotic cells are described in detail in U.S. Pat. No. 4,910,140.

NON-LIMITING EXEMPLARY EMBODIMENTS

General Recombinant DNA Techniques

Since many of the recombinant DNA techniques used in this invention are routine for the person skilled in the art, a brief description of these generally used techniques is to be given below. All these processes are described in the reference of Maniatis et al (1982), unless separate reference is made thereto.

A. Cutting with restriction endonucleases

Typically, the reaction mixture contains about 50 to 500 µg/ml DNA in the buffer solution recommended by the manufacturer, primarily New England Biolabs, Beverly, Mass. and Böhringer, Mannheim (FRG). 2 to 5 units of restriction endonucleases are added for each µg of DNA and the reaction mixture is incubated at the temperature recommended by the manufacturer for one to three hours. The reaction is stopped by heating at 65° C. for 10 minutes or by extraction with phenol, followed by precipitation of the DNA with ethanol. This technique is also described on pages 104 to 106 of the Maniatis et al (1982) reference.

B. Treatment of the DNA with polymerase in order to generate blunt ends.

50 to 500 µg/ml DNA fragments are added to a reaction mixture in the buffer recommended by the manufacturer, primarily New England Biolabs, Beverly, Mass. and Böhringer, Mannheim (FRG). The reaction mixture contains all four deoxynucleotide triphosphates in concentrations of 0.2 mM. The reaction is carried out at 15° C. for 30 minutes and is then stopped by heating at 65° C. for 10 minutes. For fragments which are obtained by cutting with restriction endonucleases which generate 5'-protruding ends, such as EcoRI and BamHI, the large fragment, or Klenow fragment, of DNA polymerase is used. For fragments which are obtained by endonucleases which generate 3'-protruding ends, such as PstI and SacI, T4 DNA polymerase is used. The use of these two enzymes is described on pages 113 to 121 of the Maniatis et al (1982) reference.

C. Agarose gel electrophoresis and purification of DNA fragments from gels

The agarose gel electrophoresis is carded out in a horizontal apparatus as described on pages 150 to 163 of the Maniatis et al. reference. The buffer used is the tris-acetate buffer described therein. The DNA fragments are stained by 0.5 µg/ml ethidium bromide which is either present in the gel or tank buffer during the electrophoresis or added after the electrophoresis. The DNA is visualised by illumination with long-wavelength ultraviolet light.

When the fragments are to be removed from the gel, the agarose used is one which gels at low temperature and can be obtained from Sigma Chemical, St. Louis, Miss. After the electrophoresis, the required fragment is cut out, placed in a plastic tube, heated at 65° C. for about 15 minutes, extracted three times with phenol and precipitated twice with ethanol. This process is a slight modification of that described by Maniatis et al (1982) on page 170.

As alternative, the DNA can be isolated from the agarose with the aid of the Geneclean kit (Bio 101 Inc., La Jolla, Calif., USA).

D. Addition of synthetic linker fragments onto DNA ends

If it is required to attach a new endonuclease cleavage site onto the end of a DNA molecule, the molecule is, where appropriate, initially treated with DNA polymerase in order to generate blunt ends as described in the above section. About 0.1 to 1.0 µg of the fragment is added to about 10 ng of phosphorylated linker DNA, which has been obtained from New England Biolabs, in a volume of 20 to 30 µl with 2 gl of T4 DNA ligase from New England Biolabs, and 1 mM ATP in the buffer recommended by the manufacturer.

After incubation at 15° C. overnight, the reaction is stopped by heating at 65° C. for 10 minutes. The reaction mixture is diluted to about 100 µl in a buffer which is correct for the restriction endonuclease which cuts the synthetic linker sequence. Approximately 50 to 200 units of this endonuclease are added. The mixture is incubated at the appropriate temperature for 2 to 6 hours, and then the fragment is subjected to an agarose gel electrophoresis and purified as described above. The resulting fragment will now have ends with endings which have been generated by cutting with the restriction endonuclease. These ends are usually cohesive so that the resulting fragment can now easily be linked to other fragments with the same cohesive ends.

E. Removal of 5'-terminal phosphates from DNA fragments

During the plasmid cloning steps, treatment of the vector plasmid with phosphatase reduces the recircularisation of the vector (discussed on page 13 of the Maniatis et al reference). After the DNA has been cut with the correct restriction endonuclease, one unit of alkaline phosphatase from the intestine of calves, which has been obtained from Boehringer-Mannheim, Mannheim, is added. The DNA is incubated at 37° C. for one hour and subsequently twice extracted with phenol and precipitated with ethanol.

F. Linkage of the DNA fragments

When fragments with complementary cohesive ends are to be linked together, about 100 ng of each fragment are incubated in a reaction mixture of 20 to 40 µl with about 0.2 units of T4 DNA ligase from New England Biolabs in the buffer recommended by the manufacturer. The incubation is carried out at 15° C. for 1 to 20 hours. When DNA fragments with blunt ends are to be linked, they are incubated as above apart from the amount of T4 DNA ligase being increased to 2 to 4 units.

G. Transformation of DNA into *E. coli*

The *E. coli* strains HB101, W3101 and ED8767 are used for most of the experiments. DNA is introduced into *E. coli* by the calcium chloride process as has been described by Maniatis et al (1982), pages 250 to 251.

H. Screening of *E. coli* for plasmids

After the transformation, the resulting colonies of *E. coli* are tested for the presence of the required plasmid by a rapid plasmid isolation process. Two usual processes are described on pages 366 to 369 of the Maniatis et al (1982) reference.

I. Isolation of plasmid DNA on a large scale

Processes for the isolation of plasmids from *E. coli* on a large scale are described on pages 88 to 94 of the Maniatis et al (1982) reference.

EXAMPLES

Example 1

Cultivation conditions for Sorangium

*Sorangium cellulosum* is cultivated in a G51b Liquid medium [see section "Media and buffers] at a temperature of 30° C. The cultures are aerated by shaking at 180 rpm. It is also possible to use a G52c medium as alternative medium.

The Sole medium described in the section "Media and buffers" can be used for the cultivation on solid medium. The incubation temperature is 30° C. in this case too.

Example 2

Cultivation conditions for *E. coli*

*E. coli* cells are cultivated in an LB medium [Miller (1972)] at a temperature of 37° C.

Example 3

Preparation of a streptomycin-resistant spontaneous mutant of *Sorangium cellulosum*

200 µl of a three-day old *Sorangium cellulosum* culture [wild-type strain So ce 26] which has been raised in liquid medium is plated out on solid medium [Sole medium] which is supplemented with 300 µg/ml streptomycin. The incubation time is 14 days at a temperature of 30° C. The colonies growing on this medium are spontaneous streptomycin-resistant mutants which are cultivated once more on the same medium (with streptomycin) for further concentration and purification.

One of these streptomycin-resistant colonies is selected and is called S J3. A sample of this mutated *Sorangium*

*cellulosum* So ce 26 strain was deposited on 25.01.1991 at the "Deutsche Sammlung von Mikroorganismen und Zellkulturen GmbH" [Braunschweig, FRG], which is recognised in accordance with the provisions of the Budapest Treaty as international depository, under deposit number DSM 6380.

Example 4

Preparation of the complete DNA of Sorangium

To isolate the complete DNA, a Sorangium culture in the stationary phase is centrifuged at 10,000 rpm for 10 minutes. The cells are removed and resuspended in STE buffer [see section "Media and buffers"] and adjusted to a cell density of about $10^9$ cells/ml.

Subsequently 450 µl of this suspension are mixed with 200 µl of RLM buffer [see section "Media and buffers"] and 2 µl of diethyl pyrocarbonate. Thorough and uniform mixing are ensured by using suitable equipment such as, for example, a Vortex or the like. After incubation in an incubator at 70° C. for 30 minutes, 100 µl of potassium acetate [5 M] are added. This mixture is incubated on ice for 15 minutes and thoroughly mixed [Vortex] every 5 minutes. After centrifugation [15 minutes at 10,000 rpm] the supernatant is subsequently mixed with 500 µl of phenol/chloroform/isoamyl alcohol [25/24/1] for extraction of the proteins. After renewed centrifugation [15 minutes at 10,000 rpm] the upper phase which contains the DNA fraction is removed, and any phenol content still present therein is removed with diethyl ether [1 ml]. The DNA is then precipitated by adding 1 mi of ethanol. After incubation at –70° C. for 30 minutes, the complete mixture is centrifuged at 10,000 rpm for 15 minutes, the pellet is washed with 70% ethanol and dried in vacuo. Finally, the DNA is dissolved in TER buffer.

Example 5

Conjugative transfer of pSJB55 into Sorangium cellulosum S J3

5.1 Two-stage process 5.1.1 Cloning of Sorangium DNA into plasmid pSUP2021

The chromosome isolated from the Sorangium S J3 strain is cut with the restriction enzyme PvuI. The fragments obtainable in this way are cloned into the plasmid pSUP2021 [Simon R. et al (1983]). This entails 0.2 µg of plasmid DNA and 1 µg of chromosomal DNA being initially digested with PvuI and subsequently precipitated with ethanol. The precipitate is removed, dried and the dried pellet is suspended in 14 µl of double-distilled water. Then 2.5 µl of a ten-fold concentrated ligation buffer [see section "Media and buffers"], 2.5 µl of bovine serum albumin [0.1%], 2.5 µl of ATP [10 mM], 2.5 µl of DTT [0.2M], 8 µl of $H_2O$ and 1 µl of T4 DNA ligase are added. The complete ligation mixture is then incubated at a temperature of about 8° C. overnight.

5 µl of this ligation mixture are transformed into the *E. coli* strain HB101 for the cloning of recombinant plasmids. For this, competent cells of the *E. coli* strain HB101 are prepared with the aid of the processes normally used for the transformation of *E. coli* [see: "General recombinant DNA techniques"].

After transformation and subsequent incubation for 24 hours on LB agar supplemented with kanamycin [25 µg/ml] and chloramphenicol [25 µg/ml], the resulting colonies are subjected to a differential screening by parallel plating out on ampicillin-containing [60 µg/ml] and ampicillin-free medium. It is subsequently possible to isolate those colonies which have lost their ampicillin resistance due to the integration of the Sorganium (sic) DNA fragments. The plasmids are then isolated from these ampicillin-sensitive colonies.

Recombinant plasmids of different size are obtained in this way. After restriction analysis, three of these plasmids are selected for further experiments. These plasmids, called pSIB50, pSIB55 and pSJB58, contain Sorangium DNA inserts of 1 Kb, 3.5 Kb and 4 Kb respectively.

5.1.2. Conjugative transfer of plasmid pSJB55 into *Sorangium cellulosum*

The transfer of plasmid pSJB55 into *Sorangium cellulosum* takes place with the mediation of *E. coli* strain W3101 (pME305) [Jaoua Set al (1987)], which is capable of a conjugation-like information exchange with Sorangium. The *E. coli* plasmid pME305 [Rella (1984)] is in this case used as helper plasmid for the mobilisation of pSJB55.

Initially, competent cells of the *E. coli* strain W3101 (pME305) are transformed, with the aid of the processes normally used for the transformation of *E. coli*, with 5 µl of the previously isolated pSJB55 plasmid DNA. The transformed *E. coli* cells are thereby becoming the donor for the plasmid pSJB55. (sic)

For the actual transfer, 15 ml of a *Sorangium cellulosum* SJ3 culture [$4\times10^8$ cells/ml to $1-4\times10^9$ cells/ml] in the stationary phase are mixed with 10 ml of a late log phase culture of *E. coli* donor cells which contain a comparable content of cells. These are then centrifuged together at 4000 to 8000 rpm for 10 minutes and resuspended in 500 µl of a G51b or G511 medium.

It has proved advantageous for the Sorangium recipient cells to be exposed briefly to a heat treatment in a waterbath before the conjugation with *E. coli*. The best transfer results with the *Sorangium cellulosum* strain S J3 can be achieved with a heat treatment at a temperature of 50° C. for 10 minutes. Under these conditions transfer frequencies of $1-5\times10^{-5}$ can be achieved, which corresponds to an increase by a factor of 10 compared with a process without previous heat treatment.

Transfer to plates with Sole solid medium is followed by a incubation at 30° C. for two days. The cells are then harvested and resuspended in 1 ml of G51b or G511 medium. 100 µl of this bacterial suspension are plated out on a selective Sole medium which, besides kanamycin [25 mg/l] also contains phleomycin [20 to 35 mg/l] and streptomycin [300 mg/1] as selective agents. Counter-selection of the donor swain [*E. coli* W3101 (pME305)] is carried out with the aid of streptomycin.

The colonies growing on this selective Sole medium after an incubation time of 10 to 14 days are transconjugants of *Sorangium cellulosum* which have acquired phleomycin resistance owing to conjugative transfer of the plasmid pSJB55. These phleomycin-resistant colonies can be used for the subsequent molecular biological investigations. The transformation frequency for the transfer of plasmid pSJB55 to Sorangium averages $3\times10^{-6}$ based on the recipient strain SJ3.

The plasmids pSJB 50 and pSJB58 can be transferred to Sorangium in an analogous manner.

5.2 One-stage process 5.2.1 Cloning of Sorangium DNA into plasmid pSUP2021

The cloning of Sorangium DNA into plasmid pSUP2021 can be carried out as described in Example 5.1.1.

Owing to the helper plasmid pME305 used in 5.1.1 being exchanged for the plasmid pUZ8 [Hedges and Matthew (1979)] which, in contrast to the abovementioned plasmid, carries no ampicillin-resistance gene, the cloning step in the *E. coli* intermediate host HB101 can be dispensed with because direct cloning in the *E. coli* donor strain ED8767 which is intended for the conjugal transfer is now possible.

The plasmid pUZ8 is a derivative of the plasmid RP4 which covers a wide host range and is described by Datta et al (1971). The modifications compared with the initial plasmid RP4 relate essentially to the ampicillin-resistance gene and to the insertion element IS21, both of which are deleted, and to the incorporation of an additional gene which confers resistance to mercury ions [see Jaoua et al (1987)].

The ligation mixture prepared as in Example 5.1.1 can therefore now be transformed directly into the *E. coli* strain ED8767. For this, competent cells of the *E. coli* strain ED8767 are prepared with the aid of the processes customarily used for the transformation of *E. coli* [see: "General recombinant DNA techniques"].

After transformation and subsequent incubation on LB agar supplemented with tetracycline [10 µg/ml] and chloramphenicol [25 µg/ml] for 24 hours, the resulting colonies are subjected to a differential screening by parallel plating out on ampicillin-containing [60 µg/ml] and ampicillin-free medium. It is subsequently possible to isolate those colonies which have lost their ampicillin resistance owing to the integration of the Sorangium DNA fragments. The cultures obtainable in this way can then be employed directly as donor cells for the conjugative transfer of recombinant plasmids into *Sorangium cellulosum* cells.

In place of the abovementioned ligation mixture, it is, of course, also possible in this case to clone the recombinant plasmids pSJB50, pSJB55 or pSJB58, prepared as in Example 5.1.1, into the *E. coli* strain ED8767.

5.2.2 Conjugative transfer of the recombinant plasmids into *Sorangium cellulosum*

For the actual transfer, 15 ml of a *Sorangium cellulosum* SJ3 culture [1–4×10$^9$ cells/ml] in the stationary phase are mixed with 10 ml of a late log phase culture of *E. coli* donor cells which contain a comparable content of cells. These are then centrifuged together at 4000 rpm for 10 minutes and resuspended in 500 µl of a G51b or G51t medium.

It proves advantageous in this case too for the Sorangium recipient cells to be exposed briefly to a heat treatment in a waterbath before the conjugation with *E. coli*. The best transfer results can be achieved with the *Sorangium cellulosum* strain S J3 with a heat treatment at a temperature of 50° C. for 10 minutes. Under these conditions, transfer frequencies of 1–5×10$^{-5}$ can be achieved, which corresponds to an increase by a factor of 10 compared with a process without previous heat treatment.

Further cultivation of the transformed Sorangium cells is carried out in analogy to the procedure described in Example 5.1.2.

Owing to the use of a restriction-negative *E. coli* strain as donor strain, such as, for example, *E. coli* ED8767 [Murray et al (1977)], the transformation frequency can be drastically increased by comparison with the process described above (up to a factor of 10$^3$).

Molecular genetic analysis (A) Detection of the integration of the plasmid pSJB55 into the chromosome of *Sorangium cellulosum* S J3

The complete DNA which has been isolated from the transformed Sorangium cells as described above [compare Example 4] is digested with SmI and SalI and loaded onto a horizontal tris-acetate [40 mM tris-HCl, 20 mM sodium acetate, 2 mM EDTANa2, pH 7.8] agarose gel [0.9%]. After the electrophoresis the gel is placed initially in a denaturing solution [1.5M NaCl, 0.5M NaOH] for 30 minutes and subsequently in a neutralising solution [1.5M NaCl, 0.5 M tris-HCl, 1 mM EDTANa2, pH 7.2]. The DNA is transferred, by means of a Southern capillary blotting, using a 20-fold concentrated SSC buffer [see section "Media and buffers"] onto a nylon membrane [for example an Amersham Hybond nylon membrane; Amersham International plc, Amersham Place, Amersham, England HP7 9NA] and fixed there by UV treatment for 6 minutes. Further details of this process are described in the Amersham International handbook "Membrane Transfer and Detection Methods", (1985).

The DNA intended as hybridisation probe is labelled by means of a nick translation [Rigby D. W. J. et al (1977)]. This takes the form of the $^{32}$P-labelled PvuI insert comprising 3.5 Kb from the plasmid pSJB55. The actual hybridisation is carried out using a slight modification of the process of Denhardt [Denhardt DT (1976)]. The buffer used for the prehybridisation and hybridisation has the following composition: 6×SSC [Maniatis et al (1982)]+5×Denhard [Maniatis et al (1982)]+0.5% SDS+0.2 mg/ml denatured salmon sperm DNA.

The prehybridisation is carried out at 65° C. and takes 3 hours, while the actual hybridisation reaction is complete after 20 hours. For the hybridisation, a $^{32}$P-labelled [10$^5$ cpm per cm$^2$ of filter], denatured PvuI fragment comprising 3.5 Kb from plasmid pSJB55 is added. After the hybridisation the filter is washed first for 2×15 minutes in 2-fold concentrated SSC at a temperature of 65° C, subsequently in 2×SSC+0.1% SDS likewise at 65° C. for 30 minutes and finally once more in 0.5×SSC [15 minutes at 65° C].

The subsequent autoradiography is carried out using an X-ray film [for example FUJY X Rays film]. The autoradiographs of the transconjugants show no bands which correspond to free pSJB55 plasmid DNA which is in over-spiralised form. By contrast, however, a positive signal is found in the chromosomal region of the filter membrane.

The SmaI-digested plasmid pSJB55 provides 3 bands of 8.9, 6.7 and 1.6 Kb. The hybridisation pattern of the parent strain S J3 after SmaI digestion likewise shows three bands, one of which corresponds to an internal fragment, comprising 1.6 Kb, of the Sorangium insert cloned into the plasmid pSJB55. The hybridisation pattern of the SmaI-digested DNA of the transconjugants shows 5 bands [8.9 and 6.7 Kb band of plasmid pSJB55 and SJ3 bands] including the 1.6 Kb band which is common to all three.

After SalI digestion, a band of 14.1 Kb is found for plasmid pSJB55 (the other SalI fragment comprising 3.1 Kb of pSJB55 does not hybridise with the probe). The hybridisation pattern of the SalI-digested S J3 DNA likewise shows a band of 5 Kb. In the transconjugants the 14.1 Kb fragment of plasmid pSJB55 and the 5 Kb fragment of SJ3 disappear after SalI digestion. These are replaced by two new bands of 11.5 Kb and 7.7 Kb.

The SmaI data show that all the pSJB55 fragments are intact in the genome of the transconjugants. This rules out the possibility of a site-specific recombination because in this case at least one of the Sinai fragments would have had to disappear. Furthermore, the results of the SaiI digestion make it clear that the plasmid pSJB55 has been integrated into the Sorangium genome, specifically at the site where the DNA region homologous with pSJB55 is located (≈3.5 Kb PvuI fragment). This integration takes place in the course of a homologous recombination between a Sorangium insert comprising 3.5 Kb from pSJB55 and the same insert within the Sorangium genome.

MEDIA AND BUFFER SOLUTIONS

G51b medium (pH 7.4)

| | |
|---|---|
| Glucose | 0.2% |
| Starch | 0.5% |
| [potato starch, Noredux type; CERESTAR ITALIA S.p.a., Milan, Italy] | |
| Peptone [DIFCO Laboratories, USA] | 0.2% |
| Probion S | 0.1% |
| [Single Cell Protein; HÖCHST AG, Frankfurt, FRG] | |
| $CaCl_2 \times 2 H_2O$ | 0.05% |
| $MgSO_4 \times 7 H_2O$ | 0.05% |
| HEPES [FLUKA] | 1.2% |

G51t medium (pH 7.4)

| | |
|---|---|
| Glucose | 0.2% |
| Starch | 0.5% |
| [potato starch, Noredux type; CERESTAR ITALIA S.p.a., Milan, Italy] | |
| Tryptone [MARCO, Hackensack, NJ USA] | 0.2% |
| Probion S | 0.1% |
| [Single Cell Protein; HÖCHST AG, Frankfurt, FRG] | |
| $CaCl_2 \times 2 H_2O$ | 0.05% |
| $MgSO_4 \times 7 H_2O$ | 0.05% |
| HEPES [FLUKA] | 1.2% |

G52c medium (pH 7.4)

| | |
|---|---|
| Glucose | 2.0 g/l |
| Starch | 8.0 g/l |
| [potato starch, Noredux type; CERESTAR ITALIA S.p.a., Milan, Italy] | |
| Soya meal defatted | 2.0 /l |
| [MUCEDOLA S.r.l., Settimo Milanese, Italy] | |
| Yeast extract | 2.0 g/l |
| [FOULD & SPRINGER, Maison Alfort, France] | |
| $CaCl_2 \times 2 H_2O$ | 1.0 g/l |
| $MgSO_4 \times 7 H_2O$ | 1.0 g/l |
| Fe-EDTA [8 g/l stock solution] | 1.0 ml |
| HEPES [FLUKA] | 2.0 g/l |
| Distilled water ad | 1000 ml |
| pH is adjusted to 7.4 with NaOH before sterilisation [20 minutes at 120° C.]. pH after sterilisation: 7.4 | |

SolE medium (pH 7.4)

| | |
|---|---|
| Glucose* | 0.35% |
| Tryptone [MARCO, Hackensack, NJ USA] | 0.05% |
| $MgSO_4 \times 7 H_2O$ | 0.15% |
| Ammonium sulfate* | 0.05% |
| $CaCl_2 \times 2 H_2O$* | 0.1% |
| $K_2HPO_4$* | 0.006% |
| Sodium dithionite* | 0.01% |
| Fe-EDTA* | 0.0008% |
| HEPES [FLUKA] | 1.2% |
| Supernatant of a sterilised, stationary S. cellulosum culture* | 3.5% (v/v) |
| Agar | 1.5% |
| *Addition takes place only after sterilisation | |
| pH is adjusted to 7.4 with NaOH before sterilisation [20 minutes at 120° C.]. | |

LB medium

| | |
|---|---|
| Tryptone | 10.0 g/l |
| Yeast extract | 5.0 g/l |
| NaCl | 5.0 g/l |

STE buffer (pH 8.0)

| | |
|---|---|
| Sucrose | 25% |
| EDTANa2 | 1 mM |
| Tris-HCl | 10 mM |

MEDIA AND BUFFER SOLUTIONS —continued

RLM buffer (pH 7.6)

| | |
|---|---|
| SDS | 5% |
| EDTANa2 | 125 mM |
| Tris-HCl | 0.5 mM |

TER buffer

| | |
|---|---|
| Tris-HCl (pH 8.0) | 10 mM |
| 1 mM EDTANa2 | 1 mM |
| RNAse | 10 μg/ml |

Ligation buffer

| | |
|---|---|
| $MgCl_2$ | 0.1 M |
| Tris-HCl (pH 7.8) | 0.5 M |

TABLES

TABLE 1

Bacterial strains and plasmids

| Strain | Relevant characteristics |
|---|---|
| *Escherichia coli* | |
| W3101Nal | RecA13, trpE, NalR |
| HB101 | F-, hsds20 (r-, m-), recA13, ara 14, proA2, lacY1, galK2, rpsL20 (SmR), xyl-5, mtl-1, sup E 44, lambda- |
| ED8767 | recA, supE, supF, hsdS |
| *Sorangium cellulosum* | |
| So ce 26 | Wild-type strain |
| So ce 26/SJ3 | SmR spontaneous mutant |
| Plasmid | |
| pSUP2021 | Ap, Cm, Km, Ph |
| pSJB50 | Cm, Km, Ph |
| pSJB55 | Cm, Km, Ph |
| pSJB58 | Cm, Km, Ph |
| pME305 | Ap, Tc |
| pUZ8 | Tc, Km, Hg |

DEPOSITION

Within the scope of the present application, the following microorganisms and plasmids have been deposited at the "Deutsche Sammlung von Mikroorganismen und Zellkulturen GmbH" in Braunschweig (FRG), which is recognised in accordance with the Budapest Treaty as international depository, to comply with the requirements for the international recognition of the deposit of microorganisms for the purpose of patenting.

| Microorganism/ plasmid | Date of deposit | Deposit number | Date of viability certificate |
|---|---|---|---|
| pSJB55 (cloned into *E. coli*) | 25.01.1991 | DSM 6321 | 25.01.1991 |
| *Sorangium cellulosum* So ce 26/SJ3 | 25.01.1991 | DSM 6380 | 14.02.1991 |

LIST OF REFERENCES

Breton A. M. et al, J Bacteriol, 161:523–528 (1985)

Breton A. M. et al, J Biotechnol, 4:303–311 (1986)

Breton A. M. and Guespin-Michel J. F., FEMS Microbiol Lett, 4–0:183–188 (1987)

Datta N. et al, J Bacteriol 108:1244–1249 (1971)

Denhardt D. T., Biochem Biophys Res Commun, 23:641–646 (1976)

Hedges R. W. and Matthew M., Plasmid 2:269–278 (1979)

Gentz R. et al, Proc Natl Acad Sci, USA 7–8:4926–4940 (1981)

Jaoua S. et al, Plasmid 18: 111–119 (1987)

Jaoua S. et al, Plasmid 23: 183–193 (1990)

Kaiser D., Genetics of Myxobacteria, in: "Myxobacteria: Development and Cell Interactions", ed E. Rosenberg, pp 163–184, Springer Verlag, Berlin/New York (1984);

Kuner Y. M. and Kaiser D., Proc Natl Acad Sci USA, 78:425–429 (1981)

Kuspa A. and Kaiser D., J Bacteriol 171:2762–2772 (1989)

Maniatis T. et al, "Molecular Cloning", Cold Spring Harbor Laboratory, Cold Spring Harbor, N.Y. (1982)

Miller J. H., "Experiments in Molecular Genetics", Cold Spring Harbor Laboratory, Cold Spring Harbor, N.Y. (1972)

Murray N. E. et al, Mol Gen Genet 150:53 (1977)

O'Conner K. A. and Zusman D. R., J Bacteriol, 155:317–329 (1983)

Rella M., Dissertation ETH Zurich, No. 7601, SFITZ

Reichenbach H. et al, Trends in Biotechnology, 6:115–121 (1988)

Rigby D. W. J. et al, J Mol Biol, 113:237–251 (1977)

Rosenberg M. and Court D., Ann Rev Genetics 13:319–353 (1979)

Shimkets L. J. et al, Proc Natl Acad Sci USA, 80:1406–1410 (1983)

Simon R. et al, Bio/Technol, November 1983:784–791 (1983)

EP 0 310 619

EP 0 358 606

U.S. Pat. No. 4,910,140

We claim:

1. A recombinant DNA molecule that integrates into the genome of *Sorangium cellulosum*, comprising:
   a first DNA sequence homologous with corresponding DNA regions in the *Sorangium cellulosum* genome, or
   a second DNA sequence flanked by flanking DNA sequences homologous with corresponding DNA regions in the *Sorangium cellulosum* genome,
   wherein said first or second DNA sequence is obtained by fragmentation of the *Sorangium cellulosum* genome, and further wherein the homology is such that upon transformation of *Sorangium cellulosum* with the recombinant DNA molecule, integration of said first or second DNA sequence by homologous recombination occurs at a site defined by the homology between the integrated DNA and the *Sorangium cellulosum* genomic DNA, independent of structural elements present on the *Sorangium cellulosum* chromosome, wherein said integration is not lethal to *Sorangium cellulosum*.

2. The recombinant DNA molecule of claim 1, wherein said homologous integrated DNA sequence is homologous with corresponding DNA regions in the *Sorangium cellulosum* genome.

3. The recombinant DNA molecule of claim 1, wherein said integrated DNA sequence is double-stranded.

4. The recombinant DNA molecule of claim 1, wherein said integrated DNA sequence is operably linked to an expression sequence functional in *Sorangium cellulosum*.

5. The recombinant DNA molecule of claim 1, wherein said integrated DNA sequence is flanked by a DNA sequence homologous to a corresponding DNA region within the *Sorangium cellulosum* genome.

6. The recombinant DNA molecule of claim 1, wherein said integrated DNA sequence originates from the target *Sorangium cellulosum* genome.

7. A cloning vector comprising the recombinant DNA molecule of claim 1.

8. A plasmid comprising the recombinant DNA molecule of claim 1 and a mobilization function active in *Sorangium cellulosum*.

9. A genetically modified *Sorangium cellulosum* cell comprising the recombinant DNA molecule of claim 1.

10. The recombinant DNA molecule of claim 5, wherein said flanking DNA sequences are linked to form a single continuous DNA molecule.

11. The genetically modified *Sorangium cellulosum* cell of claim 9, wherein said recombinant DNA molecule is integrated into the cell's genome via homologous recombination at a site defined by the homology between the DNA sequence and the corresponding regions in the genome, independent of structural elements present in the genome, or of specific transposition events.

12. A genetically modified *Sorangium cellulosum* cell comprising an exogenous DNA sequence integrated into its genome via homologous recombination.

* * * * *